US010585022B2

(12) United States Patent
Kwak et al.

(10) Patent No.: US 10,585,022 B2
(45) Date of Patent: Mar. 10, 2020

(54) COLLECTING APPARATUS FOR EXTRACELLULAR VESICLES AND METHOD FOR USING THE SAME

(71) Applicant: Korea Institute of Science and Technology, Seoul (KR)

(72) Inventors: Rhokyun Kwak, Seoul (KR); Ji Yoon Kang, Seoul (KR); Jaesung Park, Seoul (KR); Siwoo Cho, Pohang-si (KR)

(73) Assignee: Korea Institute of Science and Technology, Seoul (KR)

( * ) Notice: Subject to any disclaimer, the term of this patent is extended or adjusted under 35 U.S.C. 154(b) by 321 days.

(21) Appl. No.: 15/216,938

(22) Filed: Jul. 22, 2016

(65) Prior Publication Data

US 2017/0045430 A1     Feb. 16, 2017

(30) Foreign Application Priority Data

Aug. 11, 2015    (KR) ........................ 10-2015-0113454

(51) Int. Cl.
    *C12Q 1/68*        (2018.01)
    *G01N 1/40*        (2006.01)
              (Continued)

(52) U.S. Cl.
    CPC ................. *G01N 1/40* (2013.01); *C12Q 1/00* (2013.01); *C12Q 1/6806* (2013.01); *G01N 2001/4038* (2013.01)

(58) Field of Classification Search
    CPC . C07K 1/26; C07K 1/28; C07K 1/285; C12Q 2565/125; B01D 57/02
    See application file for complete search history.

(56) References Cited

U.S. PATENT DOCUMENTS

| 8,257,568 B1 | 9/2012 | Simmons et al. |
| 2005/0072675 A1* | 4/2005 | Dudziak ................ B01D 57/02 204/518 |

(Continued)

OTHER PUBLICATIONS

Cho, Siwoo, et al. "High Yield Extracellular Vesicle Isolation from Body Fluids by Electro-dialysis." *Isev Was Proud To Host The 2015 Annual Meeting In Washington DC, USA.* 1-30. (33 pages, in English).

(Continued)

*Primary Examiner* — Salil Jain
(74) *Attorney, Agent, or Firm* — NSIP Law

(57) ABSTRACT

Provided are an extracellular vesicle collecting apparatus using an electrode and a porous membrane and a method for using the same. The extracellular vesicle collecting apparatus includes i) an upper frame in which a pair of through holes is disposed so that a buffer solution flows therethrough, ii) a buffer tube which is inserted in the through holes and in which the buffer solution flows, iii) a positive electrode disposed on the upper frame, iv) a porous membrane located below the upper frame, v) a spacer which is located below the porous membrane and has a hollow space disposed therein, vi) a plurality of guide tubes through which a blood flows in the hollow space, vii) a lower frame which is coupled to the upper frame to be opposite to the upper frame and receives the porous membrane and the spacer therein, and viii) a negative electrode provided below the lower frame. Extracellular vesicles contained in the blood are collected by the porous membrane.

13 Claims, 6 Drawing Sheets

(51) Int. Cl.
*G01N 27/447* (2006.01)
*C12Q 1/6806* (2018.01)
*C12Q 1/00* (2006.01)

(56) References Cited

U.S. PATENT DOCUMENTS

2008/0190219 A1* 8/2008 Jensen .................... C12Q 1/04
73/864.71
2014/0187577 A1* 7/2014 Funahashi ............. A61K 31/47
514/312
2016/0216253 A1* 7/2016 Balaj .................... G01N 33/566

OTHER PUBLICATIONS

Raposo, Graca, et al. "B Lymphocytes Secrete Antigen-Presenting Vesicles." *The Journal Of Experimental Medicine* 183.3 (1996): 1161-1172. (12 pages, in English).

Davies, Ryan T., et al. "Microfluidic Filtration System To Isolate Extracellular Vesicles From Blood." *Lab on a Chip* 12.24 (2012): 5202-5210. (9 pages, in English).

Cho, Siwoo, et al. "Anodic Aluminum Oxide Membranes for Immunoisolation With Sufficient Oxygen Supply for Pancreatic Islets." Integrative Biology 5.5, 2013. (7 pages in English).

Fahrmeir, Julia, et al. "Electrophoretic Purification of Tumor-Targeted Polyethylenimine-Based Polyplexes Reduces Toxic Side Effects In Vivo." Journal of Controlled Release 122.3 (2007). (10 pages in English).

Korean Notice of Allowance dated Mar. 28, 2017 in corresponding Korean Patent Application No. 10-2015-0113454 (4 pages in Korean).

Squires, Todd M., et al."Microfluidics: Fluid Physics at the Nanoliter Scale." Reviews of modern physics 77.3 (2005) (50 pages in English).

* cited by examiner

COLLECTING APPARATUS FOR EXTRACELLULAR VESICLES AND METHOD FOR USING THE SAME

CROSS-REFERENCE TO RELATED APPLICATION

This application claims priority to and the benefit of Korean Patent Application No. 10-2015-0113454 filed in the Korean Intellectual Property Office on Aug. 11, 2015, the entire contents of which are incorporated herein by reference.

BACKGROUND OF THE INVENTION (a) Field of the Invention

The present invention relates to an extracellular vesicles collecting apparatus and a method for using the same.

(b) Description of the Related Art

Extracellular vesicles are divided into microvesicle and exosome. The extracellular vesicles serve to exchange information between cells and relate to metastasis of cancer cells, immunity, and regeneration of tissue, to serve as a biomarker.

In order to diagnose neurological diseases using blood, a separating device which separates extracellular vesicles which circulate in a blood vessel from the blood has been developed. A centrifugal separating device is an example of the separating device. The centrifugal separating device collects vesicles from nanosize materials disposed of pellets using centrifugal force. However, lots of manpower and time are required to dissolve the pellets using the centrifugal separating device. Further, the vesicles are agglomerated so that a sediment may be generated.

The above information disclosed in this Background section is only for enhancement of understanding of the background of the invention and therefore it may contain information that does not form the prior art that is already known in this country to a person of ordinary skill in the art.

SUMMARY OF THE INVENTION

An exemplary embodiment of the present invention is to provide an extracellular vesicle collecting apparatus which separates extracellular vesicles contained in blood from the blood using an electrode to which an electric field is applied and a porous membrane. An exemplary embodiment of the present invention is to provide a method for using the above-mentioned extracellular vesicle collecting apparatus.

An exemplary embodiment of the present invention provides an extracellular vesicle collecting apparatus including i) an upper frame in which a pair of through holes is disposed so that a buffer solution flows therethrough, ii) a buffer tube which is inserted in the through holes and in which the buffer solution flows, iii) a positive electrode disposed on the upper frame, iv) a porous membrane located below the upper frame, v) a spacer which is located below the porous membrane and has a hollow space disposed therein, vi) a plurality of guide tubes through which the blood flows in the hollow space, vii) a lower frame which is coupled to the upper frame to be opposite to the upper frame and receives the porous membrane and the spacer therein, and viii) a negative electrode provided below the lower frame. Herein, extracellular vesicles contained in the blood may be collected by the porous membrane.

The porous membrane may include a plurality of pores and an average diameter of the pores may be about 10 nm to about 1000 nm. An average diameter of the pores may be about 25 nm to about 50 nm. The porous membrane may include at least one material of polycarbonate, polyester, polyamide, or anodic aluminum oxide. The hollow space may include stainless steel. A diameter of the hollow space may be greater than a diameter of the guide tube. Another pair of through holes through which the buffer solution flows may be disposed on the lower frame. The apparatus may further include another buffer tube which is inserted in the through holes and in which a buffer solution flows therein.

According to the exemplary embodiment of the present invention, the extracellular vesicle collecting apparatus may further include another porous membrane located below the spacer. The positive electrode may be applied to be parallel to the porous membrane.

Another exemplary embodiment of the present invention provides a method for using an extracellular vesicle collecting apparatus including i) providing the above-described extracellular vesicle collecting apparatus, ii) applying an electric field to the positive electrode and the negative electrode, iii) injecting the buffer solution in the buffer tube, iv) injecting sample blood in the guide tube, v) moving extracellular vesicles and protein contained in the sample blood toward the positive electrode by the electric field, vi) reaching the extracellular vesicles and the protein to the porous membrane, and vii) separating the porous membrane to dissolve the adsorbed extracellular vesicles by an elution solution.

In the separating the porous membrane to dissolve the adsorbed extracellular vesicles by an elution solution, the elution solution may be a phosphate buffered saline (PBS) solution. In the reaching of the extracellular vesicles and the protein to the porous membrane, when particle sizes of the extracellular vesicles and the protein are smaller than a size of the pore of the porous membrane, the method may further include passing the extracellular vesicles and the protein through porous membrane to move to the buffer tube.

A process of collecting extracellular vesicles may be simplified using an extracellular vesicle collecting apparatus and a collecting time may be shortened. Further, the extracellular vesicles which circulate in a blood vessel may be collected at a high collection rate. Accordingly, any abnormal condition or disease of blood may be detected at an early stage.

DETAILED DESCRIPTION OF THE EMBODIMENTS

The terminologies used herein are set forth to illustrate a specific exemplary embodiment but not to limit the present invention. It must be noted that, as used in the specification and the appended claims, the singular forms include plural references unless the context clearly dictates otherwise. It will be further understood that the terms "comprises" and/or "comprising," when used in this specification, specify the presence of stated properties, regions, integers, steps, operations, elements, and/or components, but do not preclude the presence or addition of one or more other properties, regions, integers, steps, operations, elements, components, and/or groups.

Unless it is not mentioned, all terms including technical terms and scientific terms used herein have the same meaning as the meaning generally understood by the person with ordinary skill in the art to which the present invention belongs. The terms that are defined in a generally used dictionary are further understood to have the meaning that coincides with the contents that are disclosed in relating technical documents, but not as the ideal or very official meaning unless it is defined.

The present invention will be described more fully hereinafter with reference to the accompanying drawings, in which exemplary embodiments of the invention are shown. As those skilled in the art would realize, the described embodiments may be modified in various different ways, all without departing from the spirit or scope of the present invention.

Figure 1:
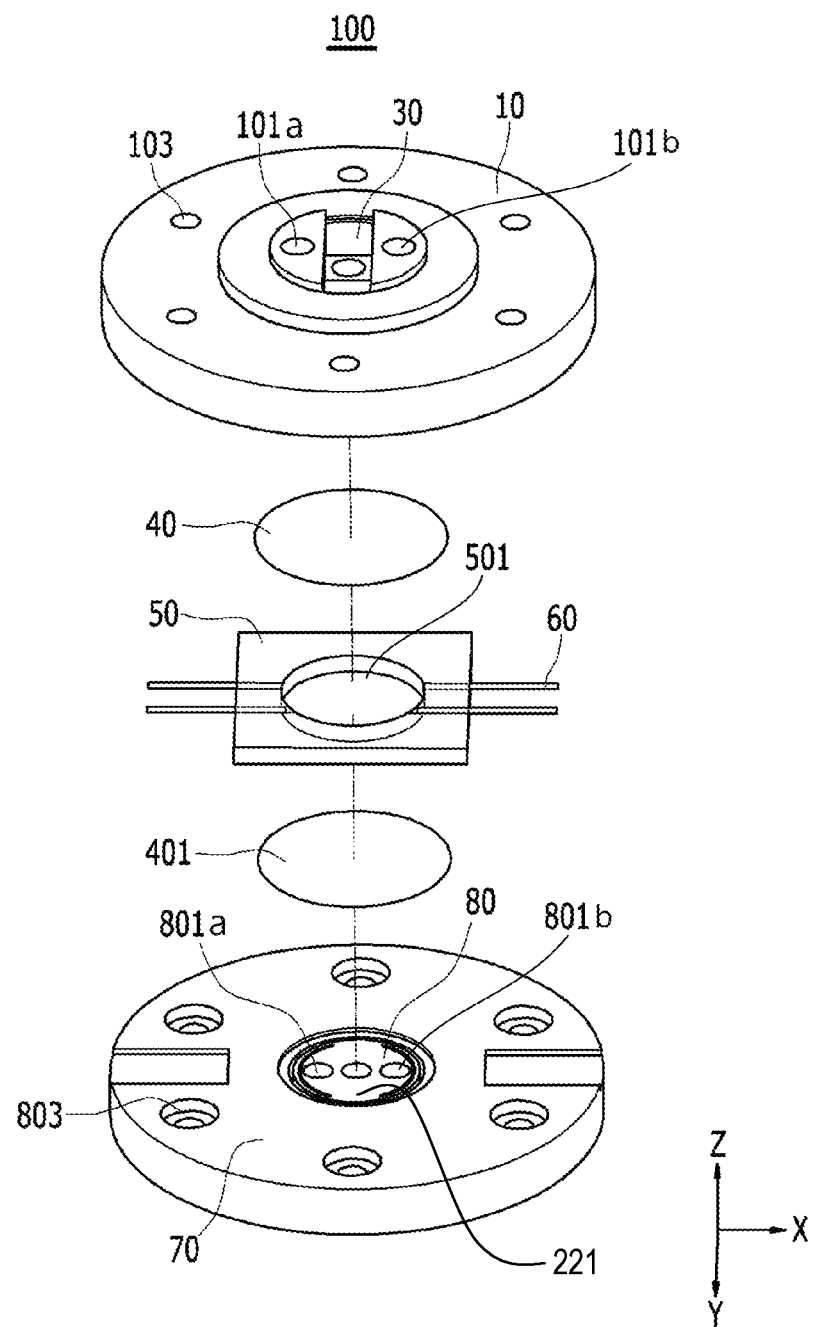
FIG. 1 is a schematic exploded view of an extracellular vesicle collecting apparatus according to a first exemplary embodiment of the present invention.

FIG. 1 schematically illustrates an extracellular vesicle collecting apparatus 100 according to a first exemplary embodiment of the present invention. A structure of the extracellular vesicle collecting apparatus 100 of FIG. 1 is provided to illustrate the present invention, but the present invention is not limited thereto. Therefore, the structure of the extracellular vesicle collecting apparatus 100 may be modified into a different structure.

As illustrated in FIG. 1, the extracellular vesicle collecting apparatus 100 includes an upper frame 10, a positive electrode 30, a porous membrane 40 or 401, a spacer 50, a guide tube 60, a lower frame 70 and a negative electrode 80. In addition, the extracellular vesicle collecting apparatus 100 may further include other components, if necessary.

A pair of through holes 101a and 101b and a space 22 (FIG. 3) are disposed in the upper frame 10. A buffer solution flows through the pair of through holes 101a and 101b and the space 22. On the upper frame 10, at least one coupling hole 103 is disposed. A coupling device (not illustrated) is inserted into the coupling hole 103 to be connected to a lower frame 70. As the coupling device, a bolt and a nut may be used. The upper frame 10 and the lower frame 70 may form appropriate stress through the coupling device. Therefore, an air-tight state may be maintained in the extracellular vesicle collecting apparatus 100.

A shaft member (not illustrated) may be inserted into the coupling hole 103. The shaft member supports the coupling state of the upper frame 10 and the lower frame 70 to reinforce the coupling structure. The positive electrode 30 is provided on the upper frame 10. The positive electrode 30 may be provided in the upper frame 10. When power is applied to the positive electrode 30, an electric field is disposed.

The porous membrane 40 is located below the upper frame 10. The porous membrane 40 includes a plurality of pores (not illustrated). An average diameter of pores may be about 10 nm to about 1000 nm. More desirably, an average diameter of pores may be about 25 nm to about 50 nm. The porous membrane 40 may be disposed of a material such as polycarbonate, polyester, polyamide, or anodic aluminum oxide. The porous membrane 40 is located to be parallel to the positive electrode 30 and the negative electrode 80. Therefore, the intensity of the electric field may be equal at all positions of the porous membrane 40. The porous membrane 40 may prevent bubbles generated in the positive electrode 30 and the negative electrode 80 from being in direct contact with the guide tube 60. That is, the porous membrane 40 may prevent the minute bubbles from hindering the collection of the extracellular vesicles in advance.

The spacer 50 is located below the porous membrane 40. The spacer 50 includes a hollow space 501 therein. The hollow space 501 may be manufactured by stainless steel. A diameter of the hollow space 501 is set to be greater than the diameter of the guide tube 60 so that the guide tube 60 may be connected to the hollow space 501. Another porous membrane 401 is located below the spacer 50. Another porous membrane 401 may be the same as the porous membrane 40.

The guide tubes 60 are connected to the hollow space 501 to allow the sample blood to flow into the hollow space 501. Two or more guiding tubes 60 may be disposed. A user may adjust the number of guide tubes 60 in accordance with an amount of the sample blood. Therefore, the guide tubes 60 may process not only a small amount of sample blood, but also a large amount of sample blood. Further, different kinds of sample bloods may flow through the guide tubes 60.

The lower frame 70 is opposite to the upper frame 10. A pair of through holes 801a and 801b and a space 221 is disposed in the lower frame 70 so that the buffer solution may flow through the through holes 801a and 801b and the space 221. At least one coupling hole 803 is disposed on the lower frame 70. That is, a coupling device is inserted in the coupling holes 103 of the upper frame 10 and the coupling holes 803 of the lower frame 70 to couple the coupling holes. Therefore, the porous membrane 40, the spacer 50, and the guide tube 60 may be disposed between the upper frame 10 and the lower frame 70.

The negative electrode 80 is provided below the lower frame 70. The negative electrode 80 may be provided in the lower frame 70. As the positive electrode 30 and the negative electrode 80, metal electrodes may be used. For example, the positive electrode 30 and the negative electrode 80 may be manufactured by a material such as copper or nickel. Hereinafter, a structure of the extracellular vesicle collecting apparatus 100 of FIG. 1 will be described in more detail with reference to FIG. 2.

Figure 2:
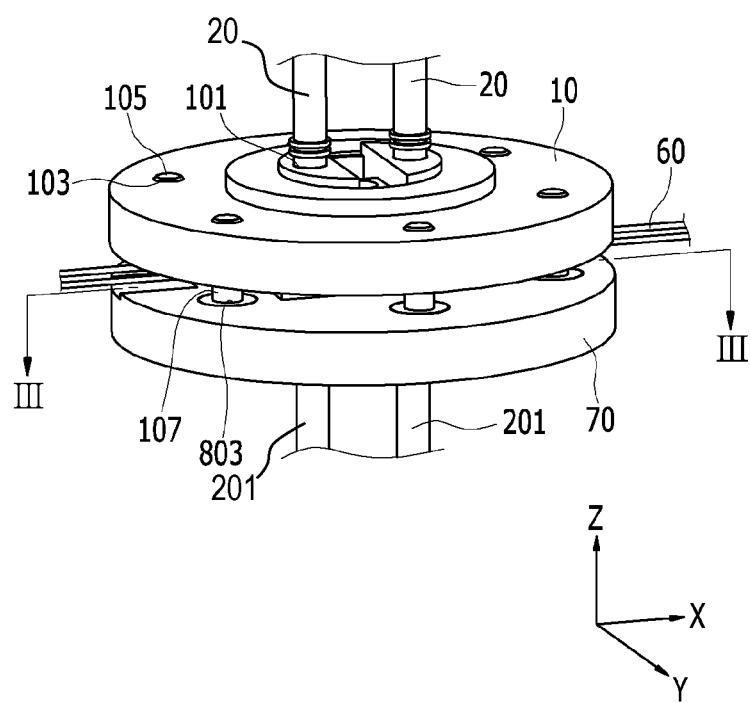
FIG. 2 is a perspective view illustrating an assembled state of an extracellular vesicle collecting apparatus of FIG. 1.

FIG. 2 is a perspective view illustrating an assembled state of an extracellular vesicle collecting apparatus 100. In FIG. 2, a structure of the extracellular vesicle collecting apparatus 100 to which buffer tubes 20 and 201 are connected is illustrated in detail.

Figure 3:
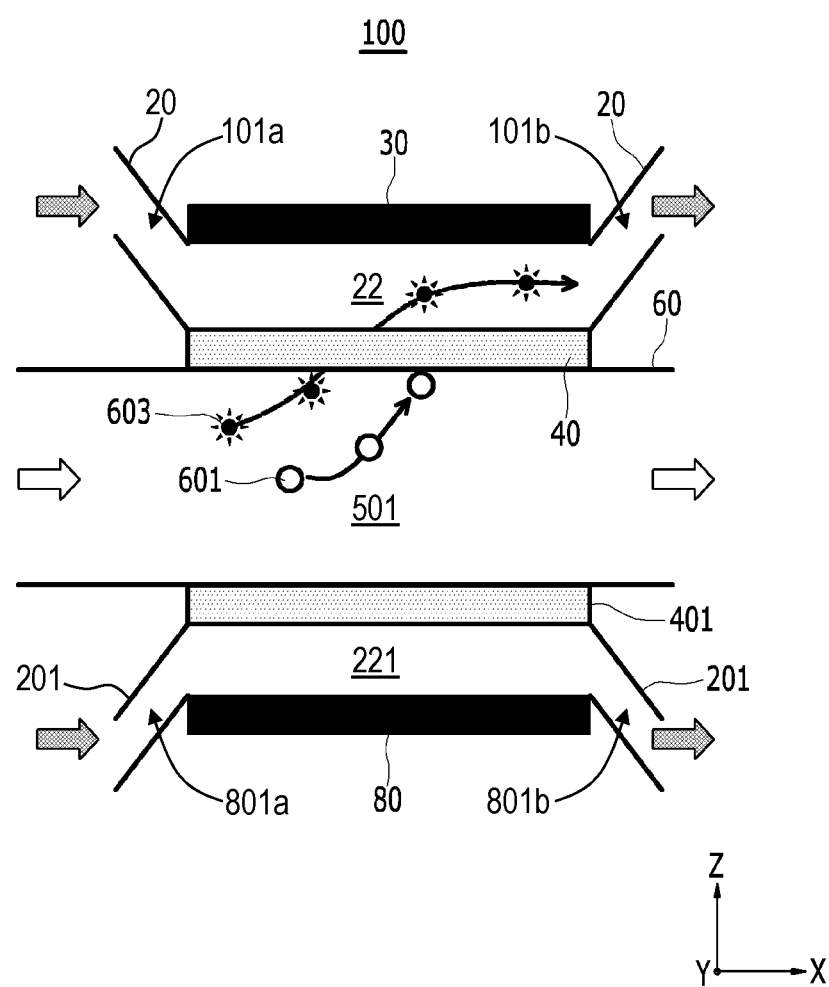
FIG. 3 is a schematic cross-sectional view of an extracellular vesicle collecting apparatus of FIG. 2, taken along the III-III line.

As illustrated in FIGS. 2 and 3, the buffer tubes 20 and 201 are inserted in the respective through holes 101a and 801a and adjacent other respective through holes 101b and 801b. The buffer solution flows through the buffer tubes 20 and 201 and spaces 22 and 221. The buffer solution may include electrolytes. Therefore, the buffer solution helps an electrode field to be transmitted from the positive electrode 30 and the negative electrode 80 to the guide tube 50 through the buffer solution. Hereinafter, an extracellular vesicle collecting process of the extracellular vesicle collecting apparatus 100 of FIG. 1 will be described in more detail with reference to FIG. 3.

FIG. 3 schematically illustrates an operating state of the extracellular vesicle collecting apparatus 100 of FIG. 2. That is, FIG. 3 schematically illustrates a cross-sectional structure of the extracellular vesicle collecting apparatus 100 taken along the III-III line of FIG. 2.

As illustrated in FIG. 3, an electric field is applied to the positive electrode 30 and the negative electrode 80. In the related art, nano-size materials are sunk using centrifugal force to obtain the extracellular vesicles. When the centrifugal force is used, as the size of particles is reduced, the centrifugal force is reduced, so that high energy is required.

In contrast, the extracellular vesicle collecting apparatus 100 may separate the extracellular vesicles using electric fields of the positive electrode 30 and the negative electrode 80 regardless of a magnitude of the force. Therefore, the extracellular vesicles may be collected with low energy consumption. The buffer solution is injected in the buffer tubes 20 and 201.

The buffer solution flows into the buffer tubes 20 and 201 and the spaces 22 and 221 along an arrow direction illustrated in the drawing. The buffer solution has a biocompatibility in which cells are survival so that the extracellular vesicles may be reused. As the buffer solution, a solution in which a buffer material is added, such as Dulbecco's modified eagle's medium (DMEM), phosphate buffered saline (PBS), Tris, or Hepes may be used. Further, a low conductive buffer material may be added to the buffer solution so as to maintain an osmotic pressure, thereby minimizing heat generated from the extracellular vesicle collecting apparatus 100 and maintaining the biocompatibility. For example, as the low conductive buffer material, sucrose and dextrose may be used.

The sample blood is injected in the hollow space 501 from the guide tube 60 to flow along the illustrated arrow direction. The sample blood contains vesicles 601 and major proteins 603. The vesicles 601 and the proteins 603 have negative charges and move to the positive electrode 30 to reach the porous membrane 40. In this case, proteins 603 which have a smaller diameter than that of the pore disposed in the porous membrane 40 pass through the porous membrane 40 to flow along the arrow direction together with the buffer solution which flows in the space 22 and the buffer tube 20. In the meantime, the vesicles 601 having a diameter which is greater than that of the pore disposed in the porous membrane 40 are adsorbed on the porous membrane 40. That is, the extracellular vesicles contained in the sample blood may be collected on the porous membrane 40.

In the related art, in the sample blood, a clot in which not only the extracellular vesicles, but also proteins and bio particles are concentrated and precipitated is agglomerated. Therefore, lots of manpower and time are required during the separating process of the extracellular vesicles.

In contrast, the extracellular vesicle collecting apparatus 100 may remove proteins and minute particles having a size of about 30 nm or smaller so that the extracellular vesicles having a high purity may be collected. The vesicles 601 collected in the porous membrane 40 may be obtained by separating the porous membrane 40 and being dissolved by an elution solution such as phosphate buffered saline (PBS).

The extracellular vesicle collecting apparatus 100 separates the vesicles and proteins from the blood sample and obtains the separated vesicles using the elution solution. Therefore, the vesicles are not chemically damaged. Further, an antigen-antibody reaction of the collecting apparatus of the related art is omitted. Therefore, activity of a surface protein of the vesicles is not lowered so that the vesicles may be reused.

Hereinafter, the present invention will be described in detail with reference to Experimental Examples. The Experimental Examples are provided to illustrate the present invention, but the present invention is not limited thereto.

Experimental Example 1

An extracellular vesicle collecting apparatus having the same structure as FIG. 2 was manufactured. A protein solution which did not include vesicles was injected in a guide tube of the extracellular vesicle collecting apparatus manufactured by the above-described method. An injecting flow rate of the protein solution was set to be 10 µm/min. As the protein solution, 40 mg/ml of bovine serum albumin which was dissolved in a DMEM buffer solution was used. Further, a low conductive buffer solution was injected in the buffer tubes of the extracellular vesicle collecting apparatus. As the low conductive buffer solution, 2385 mg/ml of HEPES, 80700 mg/ml of sucrose, and 4500 mg/ml of dextrose were used. Further, the low conductive buffer solution was mixed in the protein solution at 1:1. Further, a total mass of the protein of the protein solution which is leaked through the guide tube was observed. The remaining experiment process of the extracellular vesicle collecting apparatus may be easily understood by those skilled in the art, so that the detailed description thereof will be omitted.

Experimental Example 2

An injecting flow rate of the protein solution was set to be 20 µl/min. The remaining experiment process is the same as the above-described Experimental Example 1.

Experimental Example 3

An injecting flow rate of the protein solution was set to be 40 µl/min. The remaining experiment process is the same as the above-described Experimental Example 1.

Experimental Example 4

An injecting flow rate of the protein solution was set to be 80 µl/min. The remaining experiment process is the same as the above-described Experimental Example 1.

Experiment Results of Experimental Examples 1 to 4

Figure 4:
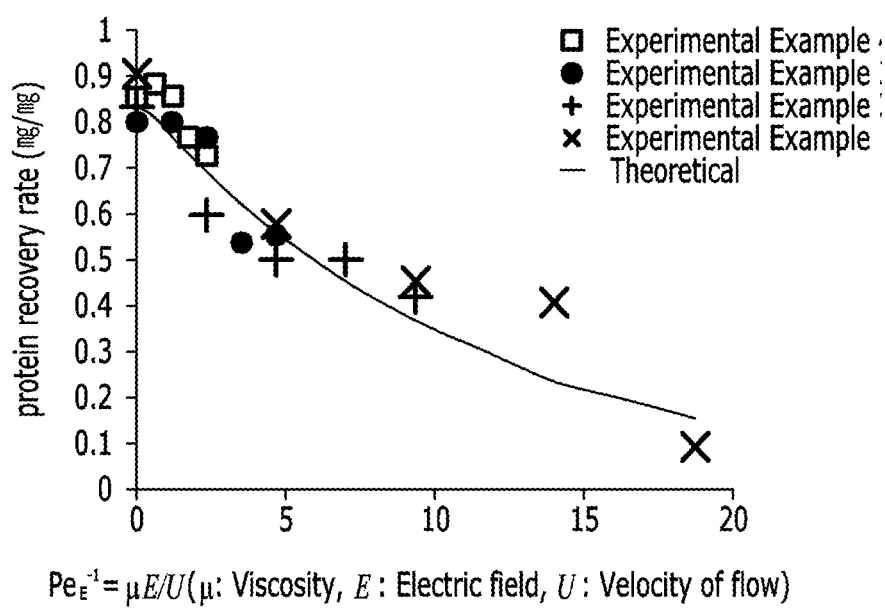
FIG. 4 is a graph of a result of a protein removal rate of an extracellular vesicle collecting apparatus according to Experimental Examples 1 to 4.

FIG. 4 is a graph of a result of a protein removal rate of an extracellular vesicle collecting apparatus according to Experimental Examples 1 to 4 of the present invention. That is, FIG. 4 illustrates a change of a leaked protein content in accordance with change of a flow rate of the protein solution which is applied to the extracellular vesicle collecting apparatus. In FIG. 4, a horizontal axis represents an inverse number of Peclet number (Pe) which is determined by a ratio of an electric field and a velocity of flow of the protein solution and a vertical axis indicates a relative ratio of a content of inflow protein solution and a protein content which is leaked through the guide tube. In FIG. 4, x indicates values of Experimental Example 1, a plus symbol indicates values of Experimental Example 2, a circle indicates values of Experimental Example 3, and a quadrangle indicates values of Experimental Example 4, and a solid line indicates a theoretical value.

As illustrated in FIG. 4, in Experimental Examples 1 to 4, it is understood that when the velocity of flow of the protein solution is slow and a voltage is high, the protein may be easily removed. Further, it is confirmed that when an inflow output of the protein solution exceeds 0.5 W, inner materials are denaturalized. Therefore, it is understood that the inflow output of the extracellular vesicle collecting apparatus needs to be adjusted to be equal to or lower than 0.5 W. It is further confirmed that an operating condition of the apparatus may be calculated using a function of the voltage and the velocity of flow.

Experimental Example 5

The extracellular vesicle collecting apparatus according to Experimental Example 1 was manufactured. A mixed solution in which 0.1 mg/ml of mouse melanoma vesicles and 40 mg/ml of bovine serum albumin protein dissolved in the DMEM buffer solution were mixed was injected in the guide tube of the extracellular vesicle collecting apparatus manufactured by the above-described method. Further, a low conductive buffer solution was injected in the buffer tubes of the extracellular vesicle collecting apparatus. The low conductive buffer solution is the same as Experimental Example 1. Further, a total mass of the protein of the mixed solution which is leaked through the guide tube and the vesicles was observed.

Experiment Result of Experimental Example 5

Figure 5:
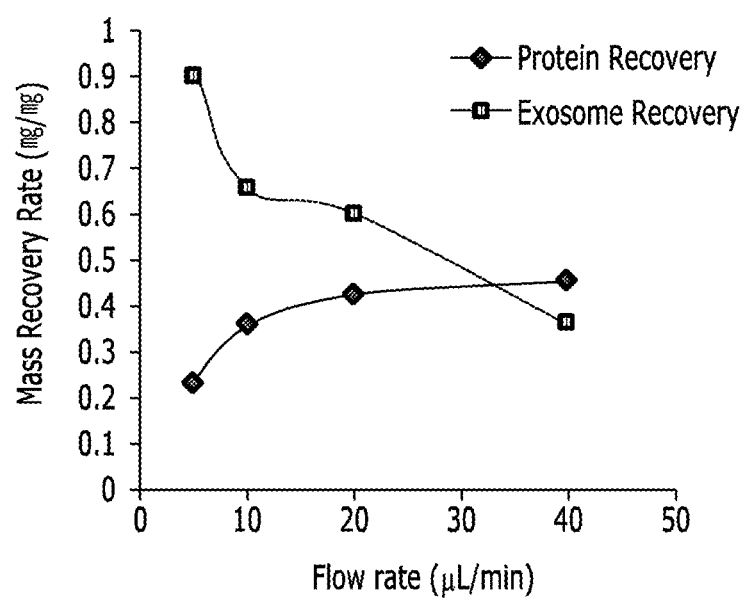
FIG. 5 is a graph of a result of a separation rate of protein and vesicles of an extracellular vesicle collecting apparatus according to Experimental Example 5.

FIG. 5 is a graph of a result of a separation rate of protein and vesicles of an extracellular vesicle collecting apparatus according to Experimental Example 5 DeletedTexts. That is, FIG. 5 illustrates a change of contents of a protein leaked through a guide tube and the vesicles in accordance with increase of a flow rate of the mixed solution which is applied to the extracellular vesicle collecting apparatus. In FIG. 5, a horizontal axis represents a flow rate and a vertical axis represents a relative ratio of protein and vesicles contents of the inflow mixed solution and protein and vesicles contents leaked through the guide tube.

As illustrated in FIG. 5, it is confirmed that as the velocity of flow of the protein is slow, a removal rate of the protein is increased and as the velocity of flow of the vesicles is slow, a yield of the vesicles is increased. Further, it is understood that a yield and purity of the vesicles may be estimated using a function of a yield and purity in accordance with the velocity of flow.

Experimental Example 6

The extracellular vesicle collecting apparatus according to Experimental Example 1 was manufactured. Mouse blood plasma was injected in the guide tube of the extracellular vesicle collecting apparatus manufactured by the above-described method. Further, the buffer solution was injected in the buffer tubes of the extracellular vesicle collecting apparatus. A protein and a total mass of RNA of the mouse blood plasma leaked through the guide tube were observed. Further, a distribution of sizes of the materials which are separated through the guide tube was measured using Dynamic light Scatter.

Comparative Example 1

An extracellular vesicle collecting apparatus (ExoQuick) which is commercially available was manufactured. The remaining experiment process is the same as the above-described Experimental Example 6.

Comparative Example 2

An extracellular vesicle collecting apparatus (Ultra) which is commercially available was manufactured. The remaining experiment process is the same as the above-described Experimental Example 6.

Experiment Result of Experimental Example 6, Comparative Examples 1 and 2

Figure 6:
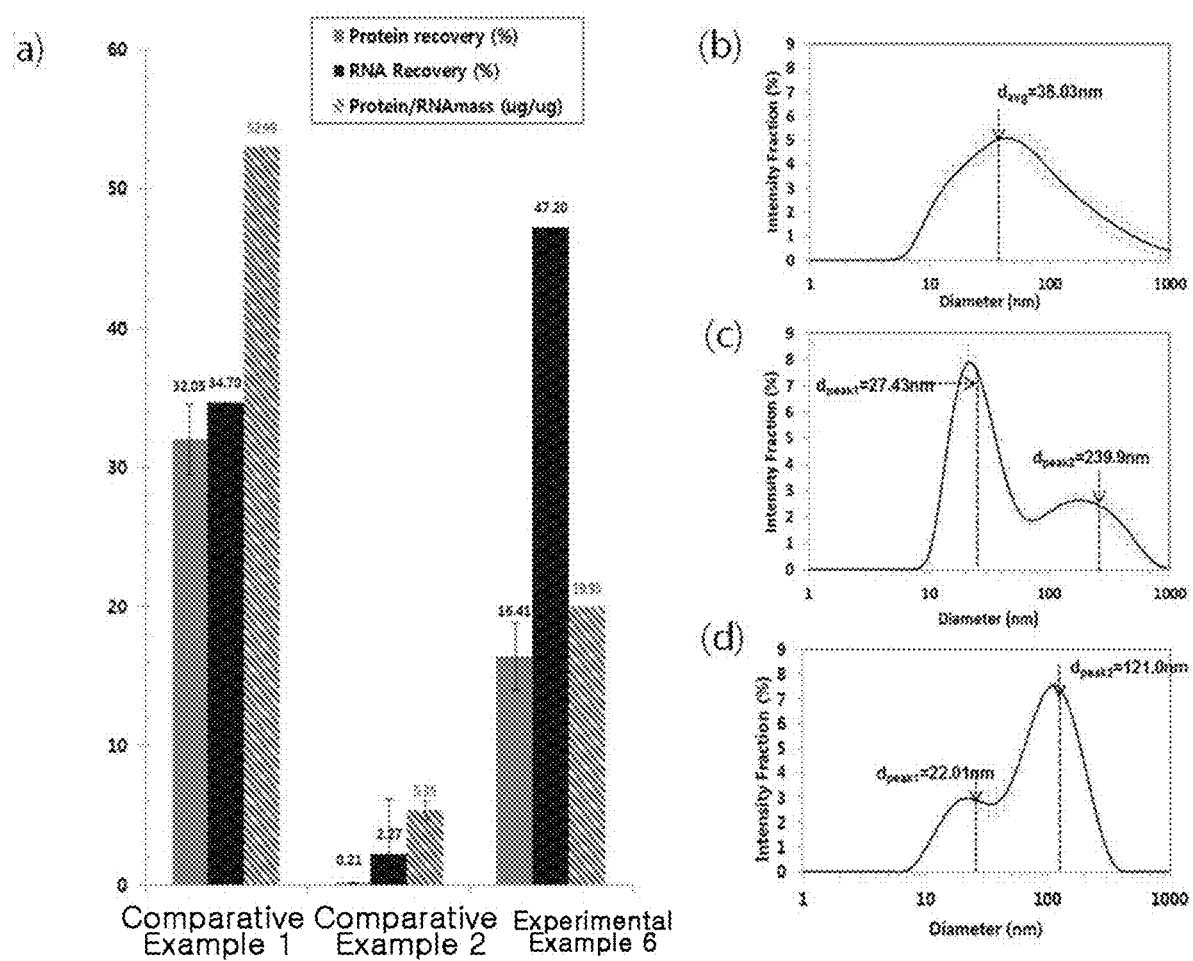
FIG. 6 is a graph of a comparison experiment of an extracellular vesicle collecting apparatus according to Experimental Example 6, Comparative Examples 1 and 2.

FIG. 6 is a graph of a result of a protein contamination level and a RNA yield of a mouse blood plasma of the extracellular vesicle collecting apparatus according to Experimental Example 6 and Comparative Examples 1 and 2 of the present invention. In FIG. 6A, protein contamination levels and RNA yields of a mouse blood plasma of the extracellular vesicle collecting apparatus according to Experimental Example 6 and Comparative Examples 1 and 2 are compared. In FIGS. 6B, 6C, and 6D, size distributions of materials separated from the extracellular vesicle collecting apparatus according to Comparative Examples 1 and 2 and Experimental Example 6 are illustrated.

As illustrated in FIG. 6A, it is understood that the RNA yield of Experimental Example 6 is the highest as compared with the RNA yields of Comparative Example 1 and Comparative Example 2. Further, it is confirmed that a protein contamination level of Experimental Example 6 is improved 60% or higher from the protein contamination level of Comparative Example 1. In FIG. 6B, a sharp peak is not shown near 100 nm corresponding to the vesicles and all sizes are evenly distributed. Therefore, it is understood that the separated materials of Comparative Example 1 are contaminated by various nanosize particles. In FIG. 6C, a peak is found near 200 nm, but the peak is relatively low. Therefore, it is understood that in Comparative Example 2, the yield is too low and a clear size distribution is not obtained. In FIG. 6D, very clear size distribution is found near 120 nm. Therefore, it is confirmed that in Experimental Example 6, the least amount of contamination due to nano particles is incurred. Further, it is understood that in Experimental Example 6, a high yield and high nanoparticle removal capacity are obtained by a short process within one hour or less per 1 ml.

The present invention has been described above. However, it is easily understood by those skilled in the art that the present invention may be changed or modified to various forms without departing from the concept and the scope of the accompanying claims.

What is claimed is:

1. An extracellular vesicle collecting apparatus, the apparatus comprising:
   an upper frame in which a pair of through holes is disposed so that a buffer solution comprising an electrolyte flows through the through holes and a space in the upper frame;
   buffer tubes which are inserted in respective ones of the through holes and in which the buffer solution flows;
   a positive electrode disposed on the upper frame;
   a porous membrane located below the upper frame;
   a spacer which is located below the porous membrane and has a cylindrical hollow space disposed therein;
   at least one guide tube connected to the cylindrical hollow space, and through the at least one guide tube a blood flows into the cylindrical hollow space;

a lower frame which is coupled to the upper frame to be opposite to the upper frame, and to hold the porous membrane and the spacer between the upper and lower frames; and a negative electrode provided below the lower frame, wherein the buffer solution flows through the upper frame space adjacent to an upper surface of the porous membrane and the hollow space is disposed adjacent to a lower surface of the porous membrane, wherein an electric field generated between the positive electrode and the negative electrode is configured to be transmitted through the buffer solution in the upper frame space, the porous membrane and the hollow space, wherein the hollow space is configured to accommodate the blood for extracellular vesicle contained in the blood having negative charge to move toward the positive electrode and reach to the porous membrane, wherein the extracellular vesicle contained in the blood having a greater diameter than a pore size of the porous membrane is filtered and collected by the porous membrane, and wherein a cross sectional area of the hollow space is greater than a sum of a cross sectional area of the at least one guide tube.

2. The apparatus of claim 1, wherein:
the porous membrane includes a plurality of pores and an average diameter of the pores is about 10 nm to about 1000 nm.

3. The apparatus of claim 2, wherein:
an average diameter of the pores is about 25 nm to about 50 nm.

4. The apparatus of claim 1, wherein:
the porous membrane includes at least one material of polycarbonate, polyester, polyamide, or anodic aluminum oxide.

5. The apparatus of claim 1, wherein:
an outer boundary of the hollow space is made of stainless steel.

6. The apparatus of claim 1, further comprising:
another pair of through holes and another space through which the buffer solution flows disposed in the lower frame; and
other buffer tubes which are inserted in respective ones of the other through holes and in which the buffer solution flows.

7. The apparatus of claim 1, further comprising:
another porous membrane located below the spacer.

8. The apparatus of claim 7, wherein:
the extracellular vesicle having positive charge and contained in the blood leaks through the at least one guide tube, moves toward the negative electrode and reaches to the other porous membrane located below the spacer.

9. The apparatus of claim 7, wherein:
the extracellular vesicle having a greater diameter than a pore size of the other porous membrane and contained in the blood is filtered and collected by the other porous membrane.

10. The apparatus of claim 1, wherein:
the positive electrode is applied to be parallel to the porous membrane.

11. A method for using the extracellular vesicle collecting apparatus of claim 1, the method comprising:
providing the extracellular vesicle collecting apparatus of claim 1;
applying the electric field to the positive electrode and the negative electrode;
injecting the buffer solution in a buffer tube of the buffer tubes;
injecting the blood in the at least one guide tube;
moving the extracellular vesicle contained in the blood toward the positive electrode by the electric field;
reaching the extracellular vesicle to the porous membrane to be filtered and collected on the porous membrane; and
separating the porous membrane from below the upper frame to dissolve the filtered and collected extracellular vesicle by an elution solution.

12. The method of claim 11, wherein:
the elution solution is a phosphate buffered saline (PBS) solution.

13. The method of claim 11, wherein:
in the reaching of the extracellular vesicles to the porous membrane,
further comprising: when particle sizes of the extracellular vesicles are smaller than the pore size of the porous membrane, passing the extracellular vesicles through porous membrane to move to the buffer tube.

* * * * *